(12) United States Patent
Gannoe et al.

(10) Patent No.: US 8,231,641 B2
(45) Date of Patent: Jul. 31, 2012

(54) METHOD AND DEVICES FOR MODIFYING THE FUNCTION OF A BODY ORGAN

(75) Inventors: Jamy Gannoe, Redwood City, CA (US); Gary Weller, Los Gatos, CA (US); Douglas S. Sutton, Pacifica, CA (US); Craig Gerbi, Mountain View, CA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1035 days.

(21) Appl. No.: 11/700,528

(22) Filed: Jan. 31, 2007

(65) Prior Publication Data

US 2007/0181138 A1    Aug. 9, 2007

Related U.S. Application Data

(63) Continuation of application No. 10/417,790, filed on Apr. 16, 2003, now Pat. No. 7,175,638.

(51) Int. Cl.
*A61B 17/08* (2006.01)
(52) U.S. Cl. .................. 606/153; 606/157
(58) Field of Classification Search .......... 606/142, 606/153, 157, 213, 215, 216; 128/898
See application file for complete search history.

(56) References Cited

U.S. PATENT DOCUMENTS

| | | | |
|---|---|---|---|
| 2,108,206 A | 2/1938 | Meeker |
| 2,508,690 A | 7/1948 | Schmerl |
| 3,372,443 A | 3/1968 | Daddona, Jr. |
| 3,395,710 A | 8/1968 | Stratton et al. |
| 3,986,493 A | 10/1976 | Hendren, III |
| 4,057,065 A | 11/1977 | Thow |
| 4,063,561 A | 12/1977 | McKenna |
| 4,133,315 A | 1/1979 | Berman et al. |
| 4,134,405 A | 1/1979 | Smit |
| 4,198,982 A | 4/1980 | Fortner et al. |
| 4,246,893 A | 1/1981 | Berson |
| 4,258,705 A | 3/1981 | Sorensen et al. |
| 4,311,146 A | 1/1982 | Wonder |
| 4,315,509 A | 2/1982 | Smit |

(Continued)

FOREIGN PATENT DOCUMENTS

EP    0 137 878 A1    4/1985

(Continued)

OTHER PUBLICATIONS

Benjamin, S.B., et al., *A Double-Blind Cross Over Study of the Garren-Edwards anti-Obesity Bubblem* Abstract Submitted to AJS/ G/E/ 1987, Georgetown University Hospital and Fairfax Hospital, Washington, D.C. and Fairfax, VA.

(Continued)

*Primary Examiner* — Gary Jackson
*Assistant Examiner* — Michael Mendoza
(74) *Attorney, Agent, or Firm* — Nutter McClennen & Fish LLP

(57) ABSTRACT

Methods and devices for partitioning or plicating a region of a hollow body organ are described herein. These methods and devices relate generally to medical apparatus and methods and more particularly to devices and methods for affecting a change in the function of a hollow body organ, particularly a stomach, intestine or gastrointestinal tract. These changes can include reducing the volume capacity of the hollow body organ, disrupting or altering the normal function of the organ, functionally excluding certain sections of the organ either by affixing adjacent tissue or excising certain regions, or affecting or correcting the response of the organ to naturally occurring stimuli, such as ingestion.

6 Claims, 6 Drawing Sheets

U.S. PATENT DOCUMENTS

| | | | |
|---|---|---|---|
| 4,343,066 A | 8/1982 | Lance | |
| 4,402,445 A | 9/1983 | Green | |
| 4,416,267 A | 11/1983 | Garren et al. | |
| 4,458,681 A | 7/1984 | Hopkins | |
| 4,485,805 A | 12/1984 | Foster, Jr. | |
| 4,501,264 A | 2/1985 | Rockey | |
| 4,547,192 A | 10/1985 | Brodsky et al. | |
| 4,558,699 A | 12/1985 | Bashour | |
| 4,592,339 A | 6/1986 | Kuzmak et al. | |
| 4,592,354 A | 6/1986 | Rothfuss | |
| 4,598,699 A | 7/1986 | Garren et al. | |
| 4,607,618 A | 8/1986 | Angelchik | |
| 4,610,383 A | 9/1986 | Rothfuss et al. | |
| 4,636,205 A | 1/1987 | Steer | |
| 4,641,653 A | 2/1987 | Rockey | |
| 4,643,169 A | 2/1987 | Koss et al. | |
| 4,646,722 A | 3/1987 | Silverstein et al. | |
| 4,648,383 A | 3/1987 | Angelchik | |
| 4,671,287 A | 6/1987 | Fiddian-Green | |
| 4,694,827 A | 9/1987 | Weiner et al. | |
| 4,696,288 A | 9/1987 | Kuzmak | |
| 4,716,900 A | 1/1988 | Ravo et al. | |
| 4,723,547 A | 2/1988 | Kullas et al. | |
| 4,739,758 A | 4/1988 | Lai et al. | |
| 4,744,363 A | 5/1988 | Hasson | |
| 4,773,393 A | 9/1988 | Haber et al. | |
| 4,790,294 A | 12/1988 | Allred, III et al. | |
| 4,795,430 A | 1/1989 | Quinn et al. | |
| 4,803,985 A | 2/1989 | Hill | |
| 4,841,888 A | 6/1989 | Mills et al. | |
| 4,899,747 A | 2/1990 | Garren et al. | |
| 4,905,693 A | 3/1990 | Ravo | |
| 4,925,446 A | 5/1990 | Garay et al. | |
| 4,927,428 A | 5/1990 | Richards | |
| 4,969,474 A | 11/1990 | Schwarz | |
| 5,037,021 A | 8/1991 | Mills et al. | |
| 5,059,193 A | 10/1991 | Kuslich | |
| 5,080,663 A | 1/1992 | Mills et al. | |
| 5,084,061 A | 1/1992 | Gau et al. | |
| 5,112,310 A | 5/1992 | Grobe | |
| 5,129,915 A | 7/1992 | Cantenys | |
| 5,146,933 A | 9/1992 | Boyd | |
| 5,156,609 A | 10/1992 | Nakao et al. | |
| 5,171,233 A | 12/1992 | Amplatz et al. | |
| 5,197,649 A | 3/1993 | Bessler et al. | |
| 5,220,928 A | 6/1993 | Oddsen et al. | |
| 5,222,961 A | 6/1993 | Nakao et al. | |
| 5,226,429 A | 7/1993 | Kuzmak | |
| 5,234,454 A | 8/1993 | Bangs | |
| 5,246,456 A | 9/1993 | Wilkinson | |
| 5,248,302 A | 9/1993 | Patrick et al. | |
| 5,250,058 A | 10/1993 | Miller et al. | |
| 5,254,126 A | 10/1993 | Filipi et al. | |
| 5,259,366 A | 11/1993 | Reydel et al. | |
| 5,259,399 A | 11/1993 | Brown | |
| 5,261,920 A | 11/1993 | Main et al. | |
| 5,263,629 A | 11/1993 | Trumbull et al. | |
| 5,284,128 A | 2/1994 | Hart | |
| 5,297,536 A | 3/1994 | Wilk | |
| 5,301,658 A | 4/1994 | Zhu et al. | |
| 5,306,300 A | 4/1994 | Berry | |
| 5,309,896 A | 5/1994 | Moll et al. | |
| 5,309,927 A | 5/1994 | Welch | |
| 5,327,914 A | 7/1994 | Shlain | |
| 5,330,486 A | 7/1994 | Wilk | |
| 5,330,503 A | 7/1994 | Yoon | |
| 5,331,975 A | 7/1994 | Bonutti | |
| 5,334,209 A | 8/1994 | Yoon | |
| 5,334,210 A | 8/1994 | Gianturco | |
| 5,345,949 A | 9/1994 | Shlain | |
| 5,346,501 A | 9/1994 | Regula et al. | |
| 5,355,897 A | 10/1994 | Pietrafitta et al. | |
| 5,376,095 A | 12/1994 | Ortiz | |
| 5,382,231 A | 1/1995 | Shlain | |
| 5,403,312 A | 4/1995 | Yates et al. | |
| 5,403,326 A | 4/1995 | Harrison et al. | |
| 5,411,508 A | 5/1995 | Bessler et al. | |
| 5,433,721 A | 7/1995 | Hooven et al. | |
| 5,437,291 A | 8/1995 | Pasricha et al. | |
| 5,449,368 A | 9/1995 | Kuzmak | |
| 5,452,837 A | 9/1995 | Williamson, IV et al. | |
| 5,458,131 A | 10/1995 | Wilk | |
| 5,462,559 A | 10/1995 | Ahmed | |
| 5,465,894 A | 11/1995 | Clark et al. | |
| 5,467,911 A | 11/1995 | Tsuruta et al. | |
| 5,486,183 A | 1/1996 | Middleman et al. | |
| 5,489,058 A | 2/1996 | Plyley et al. | |
| 5,503,635 A | 4/1996 | Sauer et al. | |
| 5,527,319 A | 6/1996 | Green et al. | |
| 5,535,935 A | 7/1996 | Vidal et al. | |
| 5,542,949 A | 8/1996 | Yoon | |
| 5,549,621 A | 8/1996 | Bessler et al. | |
| 5,551,622 A | 9/1996 | Yoon | |
| 5,555,898 A | 9/1996 | Suzuki et al. | |
| 5,558,665 A | 9/1996 | Kieturakis | |
| 5,571,116 A | 11/1996 | Bolanos et al. | |
| 5,577,654 A | 11/1996 | Bishop | |
| 5,578,044 A | 11/1996 | Gordon et al. | |
| 5,582,616 A | 12/1996 | Bolduc et al. | |
| 5,584,861 A | 12/1996 | Swain et al. | |
| 5,588,579 A | 12/1996 | Schnut et al. | |
| 5,601,604 A | 2/1997 | Vincent | |
| 5,603,443 A | 2/1997 | Clark et al. | |
| 5,607,094 A | 3/1997 | Clark et al. | |
| 5,624,381 A | 4/1997 | Kieturakis | |
| 5,626,588 A | 5/1997 | Sauer et al. | |
| 5,639,008 A | 6/1997 | Gallagher et al. | |
| 5,649,937 A | 7/1997 | Bito et al. | |
| 5,651,769 A | 7/1997 | Waxman et al. | |
| 5,655,698 A | 8/1997 | Yoon | |
| 5,662,664 A | 9/1997 | Gordon et al. | |
| 5,662,667 A | 9/1997 | Knodel | |
| 5,667,520 A | 9/1997 | Bonutti | |
| 5,676,659 A | 10/1997 | McGurk | |
| 5,676,674 A | 10/1997 | Bolanos et al. | |
| 5,685,868 A | 11/1997 | Lundquist | |
| 5,690,656 A | 11/1997 | Cope et al. | |
| 5,697,943 A | 12/1997 | Sauer et al. | |
| 5,707,382 A | 1/1998 | Sierocuk et al. | |
| 5,722,990 A | 3/1998 | Sugarbaker et al. | |
| 5,728,178 A | 3/1998 | Buffington et al. | |
| 5,735,848 A | 4/1998 | Yates et al. | |
| 5,749,893 A | 5/1998 | Vidal et al. | |
| 5,755,730 A | 5/1998 | Swain et al. | |
| 5,766,216 A | 6/1998 | Gangal et al. | |
| 5,776,054 A | 7/1998 | Bobra | |
| 5,782,844 A | 7/1998 | Yoon et al. | |
| 5,788,715 A | 8/1998 | Watson, Jr. et al. | |
| 5,792,153 A | 8/1998 | Swain et al. | |
| 5,797,931 A | 8/1998 | Bito et al. | |
| 5,810,851 A | 9/1998 | Yoon | |
| 5,810,855 A | 9/1998 | Rayburn et al. | |
| 5,810,882 A | 9/1998 | Bolduc et al. | |
| 5,816,471 A | 10/1998 | Plyley et al. | |
| 5,820,584 A | 10/1998 | Crabb | |
| 5,824,008 A | 10/1998 | Bolduc et al. | |
| 5,827,298 A | 10/1998 | Hart et al. | |
| 5,833,690 A | 11/1998 | Yates et al. | |
| 5,836,311 A | 11/1998 | Borst et al. | |
| 5,839,639 A | 11/1998 | Sauer et al. | |
| 5,860,581 A | 1/1999 | Robertson et al. | |
| 5,861,036 A | 1/1999 | Godin | |
| 5,868,141 A | 2/1999 | Ellias | |
| 5,868,760 A | 2/1999 | McGuckin, Jr. | |
| 5,876,448 A | 3/1999 | Thompson et al. | |
| 5,879,371 A | 3/1999 | Gardiner et al. | |
| 5,887,594 A | 3/1999 | LoCicero, III | |
| 5,888,196 A | 3/1999 | Bonutti | |
| 5,897,534 A | 4/1999 | Heim et al. | |
| 5,897,562 A | 4/1999 | Bolanos et al. | |
| 5,904,147 A | 5/1999 | Conlan et al. | |
| 5,906,625 A | 5/1999 | Bito et al. | |
| 5,910,105 A | 6/1999 | Swain et al. | |
| 5,910,149 A | 6/1999 | Kuzmak | |
| 5,921,993 A | 7/1999 | Yoon | |
| 5,927,284 A | 7/1999 | Borst et al. | |
| 5,928,264 A | 7/1999 | Sugarbaker et al. | |

| Patent No. | Date | Inventor |
|---|---|---|
| 5,935,107 A | 8/1999 | Taylor et al. |
| 5,938,669 A | 8/1999 | Klaiber et al. |
| 5,947,983 A | 9/1999 | Solar et al. |
| 5,964,772 A | 10/1999 | Bolduc et al. |
| 5,964,782 A | 10/1999 | Lafontaine et al. |
| 5,972,001 A | 10/1999 | Yoon |
| 5,972,002 A | 10/1999 | Bark et al. |
| 5,976,161 A | 11/1999 | Kirsch et al. |
| 5,980,537 A | 11/1999 | Ouchi |
| 5,993,464 A | 11/1999 | Knodel |
| 5,993,473 A | 11/1999 | Chan et al. |
| 6,015,378 A | 1/2000 | Borst et al. |
| 6,030,364 A | 2/2000 | Durgin et al. |
| 6,030,392 A | 2/2000 | Dakov |
| 6,042,538 A | 3/2000 | Puskas |
| 6,044,847 A | 4/2000 | Carter et al. |
| 6,067,991 A | 5/2000 | Forsell |
| 6,074,343 A | 6/2000 | Nathanson et al. |
| 6,083,241 A | 7/2000 | Longo et al. |
| 6,086,600 A | 7/2000 | Kortenbach |
| 6,113,609 A | 9/2000 | Adams |
| 6,119,913 A | 9/2000 | Adams et al. |
| 6,120,513 A | 9/2000 | Bailey et al. |
| 6,136,006 A | 10/2000 | Johnson et al. |
| 6,159,146 A | 12/2000 | El Gazayerli |
| 6,159,195 A | 12/2000 | Ha et al. |
| 6,165,183 A | 12/2000 | Kuehn et al. |
| 6,179,195 B1 | 1/2001 | Adams et al. |
| 6,186,942 B1 | 2/2001 | Sullivan et al. |
| 6,186,985 B1 | 2/2001 | Snow |
| 6,197,022 B1 | 3/2001 | Baker |
| 6,200,318 B1 | 3/2001 | Har-Shai et al. |
| 6,206,822 B1 | 3/2001 | Foley et al. |
| 6,206,893 B1 | 3/2001 | Klein et al. |
| 6,224,614 B1 | 5/2001 | Yoon |
| 6,231,561 B1 | 5/2001 | Frazier et al. |
| 6,248,058 B1 | 6/2001 | Silverman et al. |
| 6,254,642 B1 | 7/2001 | Taylor |
| 6,273,897 B1 | 8/2001 | Dalessandro et al. |
| 6,279,809 B1 | 8/2001 | Nicolo |
| 6,290,674 B1 | 9/2001 | Roue et al. |
| 6,293,923 B1 | 9/2001 | Yachia et al. |
| 6,302,917 B1 | 10/2001 | Dua et al. |
| 6,312,437 B1 | 11/2001 | Kortenbach |
| 6,328,689 B1 | 12/2001 | Gonzalez et al. |
| 6,338,345 B1 | 1/2002 | Johnson et al. |
| 6,352,543 B1 | 3/2002 | Cole |
| 6,358,197 B1 | 3/2002 | Silverman et al. |
| 6,379,366 B1 | 4/2002 | Fleischman et al. |
| 6,387,104 B1 | 5/2002 | Pugsley, Jr. et al. |
| 6,398,795 B1 | 6/2002 | McAlister et al. |
| 6,416,535 B1 | 7/2002 | Lazarus |
| 6,423,087 B1 | 7/2002 | Sawada |
| 6,432,040 B1 | 8/2002 | Meah |
| 6,447,533 B1 | 9/2002 | Adams |
| 6,460,543 B1 | 10/2002 | Forsell |
| 6,475,136 B1 | 11/2002 | Forsell |
| 6,491,707 B2 | 12/2002 | Makower et al. |
| 6,494,888 B1 | 12/2002 | Laufer et al. |
| 6,506,196 B1 | 1/2003 | Laufer |
| 6,535,764 B2 | 3/2003 | Imran et al. |
| 6,540,789 B1 | 4/2003 | Silverman et al. |
| 6,551,310 B1 | 4/2003 | Ganz et al. |
| 6,554,844 B2 | 4/2003 | Lee et al. |
| 6,558,400 B2 | 5/2003 | Deem et al. |
| 6,561,969 B2 | 5/2003 | Frazier et al. |
| 6,572,629 B2 | 6/2003 | Kalloo et al. |
| 6,579,301 B1 | 6/2003 | Bales et al. |
| 6,592,596 B1 | 7/2003 | Geitz |
| 6,605,037 B1 | 8/2003 | Moll et al. |
| 6,626,899 B2 | 9/2003 | Houser et al. |
| 6,632,227 B2 | 10/2003 | Adams |
| 6,656,194 B1 | 12/2003 | Gannoe et al. |
| 6,663,598 B1 | 12/2003 | Carrillo, Jr. et al. |
| 6,663,639 B1 | 12/2003 | Laufer et al. |
| 6,663,640 B2 | 12/2003 | Kortenbach |
| 6,675,809 B2 | 1/2004 | Stack et al. |
| 6,682,520 B2 | 1/2004 | Ingenito |
| 6,689,062 B1 | 2/2004 | Mesallum |
| 6,692,485 B1 | 2/2004 | Brock et al. |
| 6,716,222 B2 | 4/2004 | McAlister et al. |
| 6,733,512 B2 | 5/2004 | McGhan |
| 6,736,822 B2 | 5/2004 | McClellan et al. |
| 6,740,098 B2 | 5/2004 | Abrams et al. |
| 6,740,121 B2 | 5/2004 | Geitz |
| 6,746,460 B2 | 6/2004 | Gannoe et al. |
| 6,746,489 B2 | 6/2004 | Dua et al. |
| 6,754,536 B2 | 6/2004 | Swoyer et al. |
| 6,755,849 B1 | 6/2004 | Gowda et al. |
| 6,755,869 B2 | 6/2004 | Geitz |
| 6,756,364 B2 | 6/2004 | Barbier et al. |
| 6,764,518 B2 | 7/2004 | Godin |
| 6,773,440 B2 | 8/2004 | Gannoe et al. |
| 6,773,441 B1 | 8/2004 | Laufer et al. |
| 6,786,898 B2 | 9/2004 | Guenst |
| 6,790,214 B2 | 9/2004 | Kraemer et al. |
| 6,802,868 B2 | 10/2004 | Silverman et al. |
| 6,821,285 B2 | 11/2004 | Laufer et al. |
| 6,830,546 B1 | 12/2004 | Chin et al. |
| 6,835,199 B2 | 12/2004 | McGuckin, Jr. et al. |
| 6,835,200 B2 | 12/2004 | Laufer et al. |
| 6,837,848 B2 | 1/2005 | Bonner et al. |
| 6,840,423 B2 | 1/2005 | Adams et al. |
| 6,845,776 B2 | 1/2005 | Stack et al. |
| 6,896,682 B1 | 5/2005 | McClellan et al. |
| 6,916,332 B2 | 7/2005 | Adams |
| 6,926,722 B2 | 8/2005 | Geitz |
| 6,966,919 B2 | 11/2005 | Sixto, Jr. et al. |
| 6,981,978 B2 | 1/2006 | Gannoe |
| 6,991,643 B2 | 1/2006 | Saadat |
| 6,994,715 B2 | 2/2006 | Gannoe et al. |
| 7,020,531 B1 | 3/2006 | Colliou et al. |
| 7,025,791 B2 | 4/2006 | Levine et al. |
| 7,033,373 B2 | 4/2006 | de la Torre et al. |
| 7,033,378 B2 | 4/2006 | Smith et al. |
| 7,033,384 B2 | 4/2006 | Gannoe et al. |
| 7,037,343 B2 | 5/2006 | Imran |
| 7,037,344 B2 | 5/2006 | Kagan et al. |
| 7,063,715 B2 | 6/2006 | Onuki et al. |
| 7,083,629 B2 | 8/2006 | Weller et al. |
| 7,083,630 B2 | 8/2006 | DeVries et al. |
| 7,087,011 B2 | 8/2006 | Cabiri et al. |
| 7,097,650 B2 | 8/2006 | Weller et al. |
| 2001/0014800 A1 | 8/2001 | Frazier et al. |
| 2001/0020190 A1 | 9/2001 | Taylor |
| 2001/0037127 A1 | 11/2001 | De Hoyos Garza |
| 2002/0022851 A1 | 2/2002 | Kalloo et al. |
| 2002/0035361 A1 | 3/2002 | Houser et al. |
| 2002/0040226 A1 | 4/2002 | Laufer et al. |
| 2002/0047036 A1 | 4/2002 | Sullivan et al. |
| 2002/0058967 A1 | 5/2002 | Jervis |
| 2002/0072761 A1 | 6/2002 | Abrams et al. |
| 2002/0077661 A1 | 6/2002 | Saadat |
| 2002/0078967 A1 | 6/2002 | Sixto, Jr. et al. |
| 2002/0082621 A1 | 6/2002 | Schurr et al. |
| 2002/0143346 A1 | 10/2002 | McGuckin, Jr. et al. |
| 2002/0165589 A1 | 11/2002 | Imran et al. |
| 2002/0183768 A1 | 12/2002 | Deem et al. |
| 2002/0193816 A1 | 12/2002 | Laufer et al. |
| 2003/0040804 A1 | 2/2003 | Stack et al. |
| 2003/0040808 A1 | 2/2003 | Stack et al. |
| 2003/0065340 A1 | 4/2003 | Geitz |
| 2003/0065359 A1 | 4/2003 | Weller et al. |
| 2003/0093117 A1 | 5/2003 | Saadat |
| 2003/0109931 A1 | 6/2003 | Geitz |
| 2003/0109935 A1 | 6/2003 | Geitz |
| 2003/0120285 A1 | 6/2003 | Kortenbach |
| 2003/0120289 A1 | 6/2003 | McGuckin, Jr. et al. |
| 2003/0132267 A1 | 7/2003 | Adams et al. |
| 2003/0158563 A1 | 8/2003 | McClellan et al. |
| 2003/0158601 A1 | 8/2003 | Silverman et al. |
| 2003/0171760 A1 | 9/2003 | Gambale |
| 2003/0208209 A1 | 11/2003 | Gambale et al. |
| 2003/0216754 A1 | 11/2003 | Kraemer et al. |
| 2003/0225312 A1 | 12/2003 | Suzuki et al. |
| 2004/0006351 A1 | 1/2004 | Gannoe et al. |
| 2004/0009224 A1 | 1/2004 | Miller |
| 2004/0010271 A1 | 1/2004 | Kortenbach |

| | | |
|---|---|---|
| 2004/0024386 A1 | 2/2004 | Deem et al. |
| 2004/0037865 A1 | 2/2004 | Miller |
| 2004/0039452 A1 | 2/2004 | Bessler |
| 2004/0044354 A1 | 3/2004 | Gannoe et al. |
| 2004/0049209 A1 | 3/2004 | Benchetrit |
| 2004/0059349 A1 | 3/2004 | Sixto, Jr. et al. |
| 2004/0059354 A1 | 3/2004 | Smith et al. |
| 2004/0059358 A1 | 3/2004 | Kortenbach et al. |
| 2004/0082963 A1 | 4/2004 | Gannoe et al. |
| 2004/0087977 A1 | 5/2004 | Nolan et al. |
| 2004/0088008 A1 | 5/2004 | Gannoe et al. |
| 2004/0089313 A1 | 5/2004 | Utley et al. |
| 2004/0092892 A1 | 5/2004 | Kagan et al. |
| 2004/0092974 A1 | 5/2004 | Gannoe et al. |
| 2004/0097989 A1 | 5/2004 | Molina Trigueros |
| 2004/0107004 A1 | 6/2004 | Levine et al. |
| 2004/0116949 A1 | 6/2004 | Ewers et al. |
| 2004/0122456 A1 | 6/2004 | Saadat et al. |
| 2004/0122473 A1 | 6/2004 | Ewers et al. |
| 2004/0122526 A1 | 6/2004 | Imran |
| 2004/0133147 A1 | 7/2004 | Woo |
| 2004/0133238 A1 | 7/2004 | Cerier |
| 2004/0138525 A1 | 7/2004 | Saadat |
| 2004/0138526 A1 | 7/2004 | Guenst |
| 2004/0138529 A1 | 7/2004 | Wiltshire et al. |
| 2004/0138531 A1 | 7/2004 | Bonner et al. |
| 2004/0138682 A1 | 7/2004 | Onuki et al. |
| 2004/0147958 A1 | 7/2004 | Lam et al. |
| 2004/0148021 A1 | 7/2004 | Cartledge et al. |
| 2004/0148034 A1 | 7/2004 | Kagan et al. |
| 2004/0158331 A1 | 8/2004 | Stack et al. |
| 2004/0162568 A1 | 8/2004 | Saadat |
| 2004/0167546 A1 | 8/2004 | Saadat et al. |
| 2004/0172141 A1 | 9/2004 | Stack et al. |
| 2004/0181242 A1 | 9/2004 | Stack et al. |
| 2004/0193190 A1 | 9/2004 | Liddicoat et al. |
| 2004/0210243 A1 | 10/2004 | Gannoe et al. |
| 2004/0215180 A1 | 10/2004 | Starkebaum et al. |
| 2004/0225183 A1 | 11/2004 | Michlitsch et al. |
| 2004/0225194 A1 | 11/2004 | Smith et al. |
| 2004/0225305 A1 | 11/2004 | Ewers et al. |
| 2004/0236357 A1 | 11/2004 | Kraemer et al. |
| 2004/0249362 A1 | 12/2004 | Levine et al. |
| 2005/0010162 A1 | 1/2005 | Utley et al. |
| 2005/0033328 A1 | 2/2005 | Laufer et al. |
| 2005/0038415 A1 | 2/2005 | Rohr et al. |
| 2005/0049718 A1 | 3/2005 | Dann et al. |
| 2005/0055038 A1 | 3/2005 | Kelleher et al. |
| 2005/0055039 A1 | 3/2005 | Burnett et al. |
| 2005/0075622 A1 | 4/2005 | Levine et al. |
| 2005/0075653 A1 | 4/2005 | Saadat et al. |
| 2005/0080438 A1 | 4/2005 | Weller et al. |
| 2005/0080444 A1 | 4/2005 | Kraemer et al. |
| 2005/0085787 A1 | 4/2005 | Laufer |
| 2005/0096750 A1 | 5/2005 | Kagan et al. |
| 2005/0119671 A1 | 6/2005 | Reydel et al. |
| 2005/0119674 A1 | 6/2005 | Gingras |
| 2005/0143760 A1 | 6/2005 | Imran |
| 2005/0148818 A1 | 7/2005 | Mesallum |
| 2005/0149067 A1 | 7/2005 | Takemoto et al. |
| 2005/0149114 A1 | 7/2005 | Cartledge et al. |
| 2005/0177176 A1 | 8/2005 | Gerbi et al. |
| 2005/0192599 A1 | 9/2005 | Demarais |
| 2005/0192601 A1 | 9/2005 | Demarais |
| 2005/0194038 A1 | 9/2005 | Brabec et al. |
| 2005/0194294 A1 | 9/2005 | Oexle et al. |
| 2005/0194312 A1 | 9/2005 | Niemeyer et al. |
| 2005/0195925 A1 | 9/2005 | Traber |
| 2005/0195944 A1 | 9/2005 | Bartels et al. |
| 2005/0196356 A1 | 9/2005 | Leinen et al. |
| 2005/0197540 A1 | 9/2005 | Liedtke |
| 2005/0197622 A1 | 9/2005 | Blumenthal et al. |
| 2005/0197684 A1 | 9/2005 | Koch |
| 2005/0198476 A1 | 9/2005 | Gazsi et al. |
| 2005/0203547 A1 | 9/2005 | Weller et al. |
| 2005/0203548 A1 | 9/2005 | Weller et al. |
| 2005/0228415 A1 | 10/2005 | Gertner |
| 2005/0228504 A1 | 10/2005 | Demarais |
| 2005/0256533 A1 | 11/2005 | Roth et al. |
| 2005/0256587 A1 | 11/2005 | Egan |
| 2006/0020247 A1 | 1/2006 | Kagan et al. |
| 2006/0020254 A1 | 1/2006 | Hoffmann |
| 2006/0020276 A1 | 1/2006 | Saadat et al. |
| 2006/0036267 A1 | 2/2006 | Saadat et al. |
| 2006/0106288 A1 | 5/2006 | Roth et al. |
| 2006/0111735 A1 | 5/2006 | Crainich |
| 2006/0122462 A1 | 6/2006 | Roth et al. |
| 2006/0142787 A1 | 6/2006 | Weller et al. |
| 2006/0151568 A1 | 7/2006 | Weller et al. |

FOREIGN PATENT DOCUMENTS

| | | |
|---|---|---|
| EP | 0 174 843 A1 | 3/1986 |
| EP | 0 246 999 A1 | 11/1987 |
| EP | 0 540 010 A2 | 5/1993 |
| JP | 63277063 A | 11/1988 |
| JP | 63279854 | 11/1988 |
| JP | 63302863 A | 12/1988 |
| JP | 01049572 A | 2/1989 |
| JP | 04297219 | 10/1992 |
| WO | WO 94/18893 A1 | 9/1994 |
| WO | WO 99/17662 A1 | 4/1999 |
| WO | WO 99/53827 A1 | 10/1999 |
| WO | WO 00/32137 A1 | 6/2000 |
| WO | WO 00/39708 A1 | 7/2000 |
| WO | WO 00/48656 A1 | 8/2000 |
| WO | WO 00/78227 A1 | 12/2000 |
| WO | WO 00/78229 A1 | 12/2000 |
| WO | WO 01/66018 A1 | 9/2001 |
| WO | WO 01/67964 A2 | 9/2001 |
| WO | WO 01/85034 A1 | 11/2001 |
| WO | WO 02/24080 A2 | 3/2002 |
| WO | WO 02/35980 A2 | 5/2002 |
| WO | WO 02/39880 A2 | 5/2002 |
| WO | WO 02/071951 A1 | 9/2002 |
| WO | WO 02/091961 A1 | 11/2002 |
| WO | WO 02/096327 A2 | 12/2002 |
| WO | WO 03/007796 A2 | 1/2003 |
| WO | WO 03/017882 A2 | 3/2003 |
| WO | WO 03/078721 A2 | 9/2003 |
| WO | WO 03/086247 A1 | 10/2003 |
| WO | WO 03/088844 A1 | 10/2003 |
| WO | WO 03/094785 A1 | 11/2003 |
| WO | WO 03/099140 A1 | 12/2003 |
| WO | WO 03/105563 A2 | 12/2003 |
| WO | WO 03/105671 A2 | 12/2003 |
| WO | WO 2004/009269 A2 | 1/2004 |
| WO | WO 2004/014237 A1 | 2/2004 |
| WO | WO 2004/017863 A2 | 3/2004 |
| WO | WO 2004/019787 A2 | 3/2004 |
| WO | WO 2004/019826 A1 | 3/2004 |
| WO | WO 2004/037064 A2 | 5/2004 |
| WO | WO 2004/049911 A2 | 6/2004 |
| WO | WO 2004/058102 A2 | 7/2004 |
| WO | WO 2004/060150 A1 | 7/2004 |
| WO | WO 2004/087014 A2 | 10/2004 |
| WO | WO 2004/103189 A1 | 12/2004 |
| WO | WO 2005/023118 A1 | 3/2005 |
| WO | WO 2005/037152 A1 | 4/2005 |
| WO | WO 2005/058239 A2 | 6/2005 |
| WO | WO 2005/060882 A1 | 7/2005 |
| WO | WO 2006/078781 A1 | 7/2006 |

OTHER PUBLICATIONS

Benjamin, S.B., *Small Bowel Obstruction and the Garren-Edwards Bubble, Lessons to be Learned?* Abstracts Submitted to A/S/G/E 1987, Division of Gastroenterology, Department of Medicine, Georgetown University Hospital, Washington, D.C.

Boyle, Thomas M., M.D., et al., Small Intestinal Obstruction Secondary to Obturation by a Garren Gastric Bubble, *The American Journal of Gastroenterology*, vol. 82, No. 1, pp. 51-53, 1987.

Büchler, M.W., M.D. et al., A Technique for Gastroplasty as a Substitute for the Esophagus: Fundus Rotation Gastroplasty, *Journal of The American College of Surgeons*, vol. 182, pp. 241-245, Mar. 1996.

Cass, O.W., et al., *Long-Term Follow-Up of Patients With Percutaneous Endoscopic Gastrostomy (PEG)*, Abstracts Submitted to A/S/G/E 1987, Department of Medicine, Hennepin County Medical Center, Minneapolis, MN 55415.

Chang, Craig G. M.D.[1], et al.. Gastro-Clip® Gastroplasty: A Very Long-Term Complication, *Obesity Surgery*, 14, © FD-Communications Inc.. 2004.

Clark, Charlene, R.N., The Gastric Bubble: Medicine, Magic or Mania? *SGA Journal*, vol. 9, No. 2, pp. 45-47, Fall 1986.

Cummings, David E., M.D., et al., Plasma Ghrelin Levels After Diet-Induced Weight Loss or Gastric Bypass Surgery, *New England Journal of Medicine*, vol. 346, No. 21, pp. 1623-1630, May 23, 2002.

Davenport, Horace W., Ph.D., D.Sc., *Physiology of the Digestive Tract: An Introductory Text*, 3d Ed., Cover and Table of Contents.

DeMeester, Tom T., M.D., Evolving Concepts of Reflux: The Ups and Downs of the LES, *Canadian Journal of Gastroenterology*, vol. 16, No. 5, pp. 327-331, 2002.

De Waele, B., M.D., et al., Intragastric Balloons for Preoperative Weight Reduction, *Obesity Surgery*, vol. 10, pp. 58-60, 2000.

Edell, Steven L., et al., Radiographic Evaluation of the Garren Gastric Bubble, *American Journal of Radiology*, vol. 145, pp. 49-50, Jul. 1985.

Endo Gia* Universal, Single UseStapler and Endo GIA Roticulator*, Brochure, 8 pages, Undated.

Filipi, Charles J. M.D., et al., Transoral, Flexible Endoscopic Suturing for Treatment of GERD: A Multicenter Trial, *Gastrointestinal Endoscopy,*. vol. 53, No. 4, pp. 416-422, 2001.

Gray, Henry, R. R.S., *Anatomy of the Human Body*, The Digestive System, Thirtieth American Edition, pp. 1466-1467 (Undated).

Guidant, Internet, AXIUS™ VACUUM 2 Stabilizer Systems, Internet Website—www.guidant.com/products/axius_vacuum.shtml, 8 pages, visited May 27, 2003.

Gukovsky-Reicher, S., M.D. et al., *Expandable Metal Esophageal Stents: Efficacy and Safety. Review of Current Literature Data and of 53 Stents Placed at Harbor-UCLA Medical Center*, www.medscape.com/viewarticle/423508_print pp. 1-20, Medscape General Medicine 4(1), 2003 © 2002 Medscape, downloaded Oct. 9, 2006.

Hepworth, Clive C. FRCS et al., Mechanical Endoscopic Methods of Haemostasis for Bleeding Peptic Ulcers: A Review, *Bailliere's Clinical Gastroenterology*, vol. 14, No. 3 pp. 467-476, 2000.

Ikeda, Y. et al., New Suturing Device for Transanal Endoscopic Microsurgery, *Blackwell Science Ltd*. p. 1290, 1997.

Johnson & Johnson Gateway[sm] Endopath 3mm, 5mm and 10 mm Diameter Endoscopic Instruments, Internet Website—www.inigateway.com/home.ihtml?loc=USENG&page=viewContent&parentId-0900..., 3 pages, visited May 29, 2003.

Kirby, Donald F., Incomplete Small Bowel Obstruction by the Garren-Edwards Gastric Bubble Necessitating Surgical Intervention, *The American Journal of Gastroenterology*, vol. 82, No. 3, pp. 251-253, 1987.

Nieben, Ole Gyring, et al., Intragastric Balloon as an Artificial Bezoar for Treatment of Obesity, *The Lancet*, pp. 198-199, Jan. 23, 1982.

Percival, Walter L., M.D., "The Balloon Diet": A Noninvasive Treatment for Morbid Obesity. Preliminary Report of 1908 Patients, *The Canadian Journal of Surgery*, vol. 27, No. 2, pp. 135-136.

Power Medical Interventions Digital and Wireless Medical Technology, Product Innovation: SurgASSIST™, Internet Website—www/pmi2.com/access_flexibility.asp, 6 pages, visited May 29, 2003.

Snowden Pencer, Diamon-Flex Angled Snake Retractor, Appendix F.f, Undated.

Stoltenberg, P.H., et al., *Intragastric Balloon Therapy of Obesity: A Randomized Double-Blind Trial*, Abstracts of Papers 1985, Scott & White Clinic, Texas A&M College of Medicine, Temple, Texas.

Swain, C. Paul, M.D., An Endoscopic Sewing Machines, *Gastrointestinal Endoscopy*, vol. 32, No. 1 pp. 36-38 1986.

Swain, C. Paul, M.D. et al., An Endoscopic Sewing and Stapling Machine, *Endoscopy* pp. 205-210, © Georg Thieme Verlag Stuttgart, New York, 1997.

Swain, C. Paul, M.D., An Endoscopic Stapling Device: The Development of a New Flexible Endoscopically Controlled Device for Placing Multiple Transmural Staples in Gastrointestinal Tissue, *Gastrointestinal Endoscopy*, vol. 35, No. 4, pp. 338-339, 1989.

Swain, C. Paul, M.D., Endoscopic Suturing, *Bailliere's Clinical Gastroenterology*, Bailliere's Tindall, vol. 13 No. 1, pp. 97-108, 1999.

Taylor, T. Vincent, et al., Gastric Balloons for Obesity, *The Lancet*, Abstract, Mar. 27, 1982.

Vandenplas, Y., et al., Intragastric Balloons in Adolescents With Morbid Obesity, *European Journal of Gastroenterology & Hepatology*, vol. 11, No. 3, pp. 243-245, 1999.

Villar, Hugo V., M.D., et al., Mechanisms of Satiety and Gastric Emptying After Gastric Partitioning and Bypass, *Surgery*, pp. 229-236, Aug. 1981.

Wullstein, C., et al., Compression Anastomosis (AKA-2) in Colorectal Surgery: Results in 442 Consecutive Patients, *British Journal of Surgery 2000*, pp. 1071-1075.

METHOD AND DEVICES FOR MODIFYING THE FUNCTION OF A BODY ORGAN

This application is a continuation of U.S. Ser. No. 10/417,790, now U.S. Pat. No. 7,175,638, filed Apr. 16, 2003, the contents of which are incorporated herein by reference.

FIELD OF THE INVENTION

The present invention relates generally to medical apparatus and methods and more particularly to devices and methods for affecting a change in the function of a hollow body organ. These changes can include, for example, reducing the volume capacity of the hollow body organ, disrupting or altering the normal function of the organ, functionally excluding certain sections of the organ either by affixing adjacent tissue or excising certain regions, or affecting or correcting the response of the organ to naturally occurring stimuli, such as ingestion.

Reducing the volume of a hollow body organ by partitioning or plicating the organ, such as the stomach, results in a smaller reservoir within the organ that can hold only a reduced amount of food and thereby induce weight loss. In addition, such partitioning or plicating of the stomach may also prove efficacious for weight loss by affecting or interfering with stomach motility and/or decreasing gastric emptying time by reducing the organ's pumping efficiency in a variety of ways. For instance, excluding the fundus of the stomach may thereby decrease the pressure waves it generates and/or interfere with the muscular region of stomach (antrum) to slow pumping. In this way, the devices and methods disclosed herein can effect or correct the response of the organ to naturally occurring stimuli. A further effect of partitioning or plicating tissue in the stomach may relate to the treatment of gastro esophageal reflux disease or "GERD" by pinning the walls of the stomach together and thereby altering stomach distension and the related "unrolling" of the lower esophageal sphincter (LES). Yet another effect of a single plication or series of plications may include causing scarring and stiffening of the region to similarly resist unrolling. Additionally, the methods and devices disclosed herein can exclude regions of the stomach organ, such as the fundus, to reduce capacitance, or to eliminate excretion of certain substances such as Ghrelin, the hormone closely associated with increased food intake.

The devices and methods disclosed herein may be used alone or in conjunction with each other. Furthermore, the devices may be permanently implanted or removed once they have served their purpose, e.g., the desired tissue effect has occurred (healing), or the clinical benefit has been achieved, for example, the patient has lost the directed or desired amount of weight, or the patient is no longer experiencing reflux.

BACKGROUND OF THE INVENTION

The current methods of treatment for gastrointestinal disorders, such as GERD, include medical intervention (drug therapy) or stimulation of lower esophageal region with RF or other energy. While effective to a certain degree, a more robust intervention would be desirable to achieve a longer term and more effective result.

In the case of severe obesity, patients may currently undergo several types of surgery either to tie off or staple portions of the large or small intestine or stomach, and/or to bypass portions of the same, e.g., to reduce the amount of food desired by the patient, and/or to reduce the amount of food absorbed by the gastrointestinal tract. Typically, these stomach reduction procedures are performed surgically through an open incision and staples or sutures are applied externally to the stomach or hollow body organ; however, several limitations exist due to the invasiveness of the procedures, including, e.g., time, use of general anesthesia, healing of the incisions, and other complications attendant to major surgery.

There is a need for improved devices and procedures in treating both gastrointestinal disorders and severe obesity. In addition, because of the invasiveness of many of the conventional surgical procedures used to manipulate, in particular, the stomach, there remains a need for improved devices and methods for more effective, less invasive intragastric restriction or partitioning procedures.

SUMMARY OF THE INVENTION

The methods and devices employed to achieve the results disclosed herein are further set forth in U.S. patent application Ser. No. 09/871,297 filed May 30, 2001, and U.S. patent application Ser. No. 10/188,547 filed Jul. 2, 2002, both fully incorporated herein by reference in their entirety. Accordingly, placement of intragastric partitions by the use of such devices and methods can be employed from within the gastric cavity to result in varying tissue geometries depending on the desired effect. The terms "plication", "partition", "fastening line", and "barrier" shall all refer to a zone where tissue folds or layers from adjacent or opposing regions of a hollow organ have been acquired and fixed so as to heal into a fused zone.

In one aspect, a variety of organ partitions or plications may be placed within the organ cavity to serve as barriers or "pouches" that are substantially separated from the majority of the organ cavity. For example, in the case where the stomach is partitioned, the "pouch" walls or partitions may be created just below the esophagus to reduce the volume of the stomach. This procedure has the effect of not only reducing the volume of food that can be consumed by the patient, but also blocks, in the similar way a valve or splash might, the volume of any refluxant material that can contribute to GERD.

In another aspect, multiple partition lines or plications can be created and positioned to impact the motility of the organ in addition to reducing the effective volume of the body organ in which they are placed. In the case of a stomach, a reduction in motility has been shown to affect satiety and also the rate of gastric emptying, which in turn leads to less food intake and subsequent weight loss. (Villar, et al. Mechanisms of satiety and gastric emptying after gastric portioning and bypass, Surgery, August 1981 229-236.) The stomach may essentially be divided into two regions on the basis of its motility pattern. The upper stomach; including the fundus and upper stomach body, exhibits low frequency, sustained contractions that are responsible for generating a pressure within the stomach. The lower stomach, composed of the lower body and antrum, develops strong peristaltic waves of contraction. These powerful contractions constitute a very effective gastric pump. Gastric distention increases fundic activity and thus stimulates this type of contraction, thereby accelerating gastric emptying.

Disrupting this motility pattern can subdue or otherwise attenuate contraction waves initiated by the fundus of the stomach in response to distension. Such contractions in a non-partitioned stomach would transmit to the antrum of the stomach and facilitate gastric digestion and drainage. (Davenport Physiology of the digestive tract, 3.sup.rd Ed. 1971, Yearbook Medical Publishers, Chicago.) However, in a partitioned stomach, the contractions are decreased and/or the food passage pathways are attenuated by plications or fixation lines. As a further result, communication with the antrum and other stomach regions is less efficient as is the communication between the antrum and the small intestine, thereby leading to a reduced rate of emptying. Furthermore, smaller pouches or multiple partitions within the stomach may also increase the pressure experienced by the fundus (fundic pressure) thereby enhancing the feeling of satiety with a lower volume of food.

In another aspect, it may be desirable to place a partition or plication to exclude the fundic region of the stomach organ from the other functioning regions to minimize the overall volume of the organ so as to limit food intake. Additionally, the plication or plications may be placed at the region of the stomach responsible for the secretion of certain "hunger hormones" to impair secretion and thereby control the impact of these hormones on hunger. Ghrelin, for instance, is a hormone produced primarily by the stomach (more concentrated in the fundic region) that has been shown to increase food intake. A marked suppression of Ghrelin levels has been correlated to the exclusion of large portions of the stomach following gastric bypass, thus contributing to the long term weight loss of a patient from such a procedure. (Cummings et al., Plasma Ghrelin Levels after Diet-Induced Weight Loss of Gastric Bypass Surgery, NEJM, Vol 346:1623-1630, May 23, 2002.)

In yet another aspect, a partition line or plication may be placed substantially parallel to the lesser curve (LC) of the stomach organ, preferably just below the lower esophageal sphincter (LES) between the lesser curve (LC) and the greater curve (GC). Such a plication can function to reinforce the LES and therefore prevent its elongation or "unrolling" when the stomach organ distends in response to food or liquid intake.

When a patient experiences GERD, it may be associated with the LES being rendered incompetent. When the LES becomes incompetent, it fails to perform its valving or barrier function against the flow of gastric juices back into the esophagus from the higher pressure environment of the stomach. It has been documented that the overall length of the LES is critically important to its function as such a barrier. (DeMeester, Evolving Concepts of Reflux: The ups and downs of the LES, Can. J. Gastroenterol 2002; 16(5):327-331.) Typically, the LES shortens as a natural response to gastric distension, such as when food is ingested into the stomach. If the LES is compromised or weakened, such distension can lead to the LES shortening or "unrolling" to the extent that it can no longer overcome pressure against it from the gastric cavity. This may result in refluxant from the gastric cavity entering the esophageal reservoir. Acutely, such contact can cause severe discomfort and other symptoms, and over time, can lead to serious complications such as cancer, ulcerations, esophagitis, Barrett's Esophagus etc.

A plication placed just below the LES within the gastric cavity, as referenced above, works to prevent the shortening or unrolling of the LES by stabilizing the region. The anterior and posterior walls of the gastric cavity may be fixed together to minimize the distension of the region in response to gastric filling. It is also possible to plicate adjacent walls such as the anterior wall of the stomach or posterior wall of the stomach to the LC or GC, walls from the GC to walls from the GC, or other combinations thereof. Such a plication can be placed substantially parallel with the LC of the stomach so as not to affect the volume of food intake for a patient Alternatively, the plication can also be placed more horizontally if both stabilization and volume reduction of the region are desired. Certain tools have been employed to create an artificial sphincter such as those described in U.S. Pat. Nos. 6,475,136, and 6,254,642. Additionally, several devices have been suggested to plicate various regions of an organ, such as those described in U.S. Pat. Nos. 5,403,326; 5,355,897; 5,676,674; 5,571,116; 6,447,533; 6,086,600; and Publications WO 02/24080; WO 01/85034; US 2002/0078967; and US 2002/0,072,761.

DETAILED DESCRIPTION OF THE INVENTION

The present invention provides, in part, for methods and devices to manipulate, partition, divide or restrict a hollow organ and, more particularly, provides methods and devices to treat diseases, such as obesity and gastroesophageal reflux disease (GERD), that can be mediated by the gastrointestinal organs.

Figure 1:
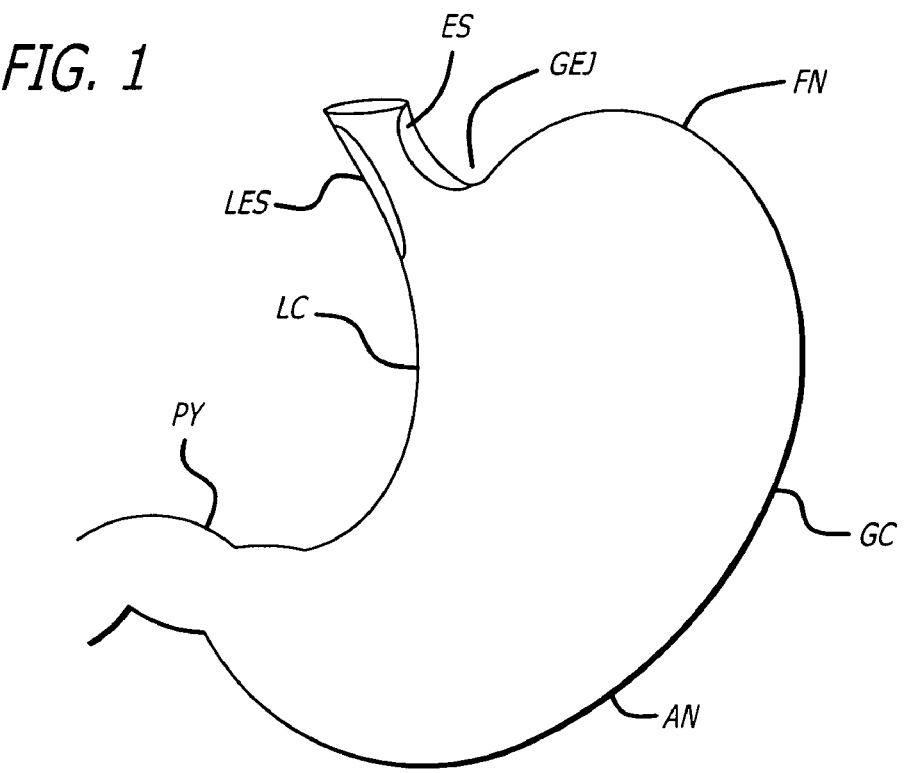
FIG. 1 depicts various anatomical locations with respect to the gastrointestinal tract.

FIG. 1 depicts an external view of various anatomical locations related to the gastrointestinal tract, including the esophagus (ES), lower esophageal sphincter (LES), gastroesophageal junction (GEJ), lesser curve (LS) of the stomach, greater curve (GC) of the stomach, fundic region of the stomach or fundus (FN), antrum of the stomach (AN), and pylorus (PY).

Figure 2:
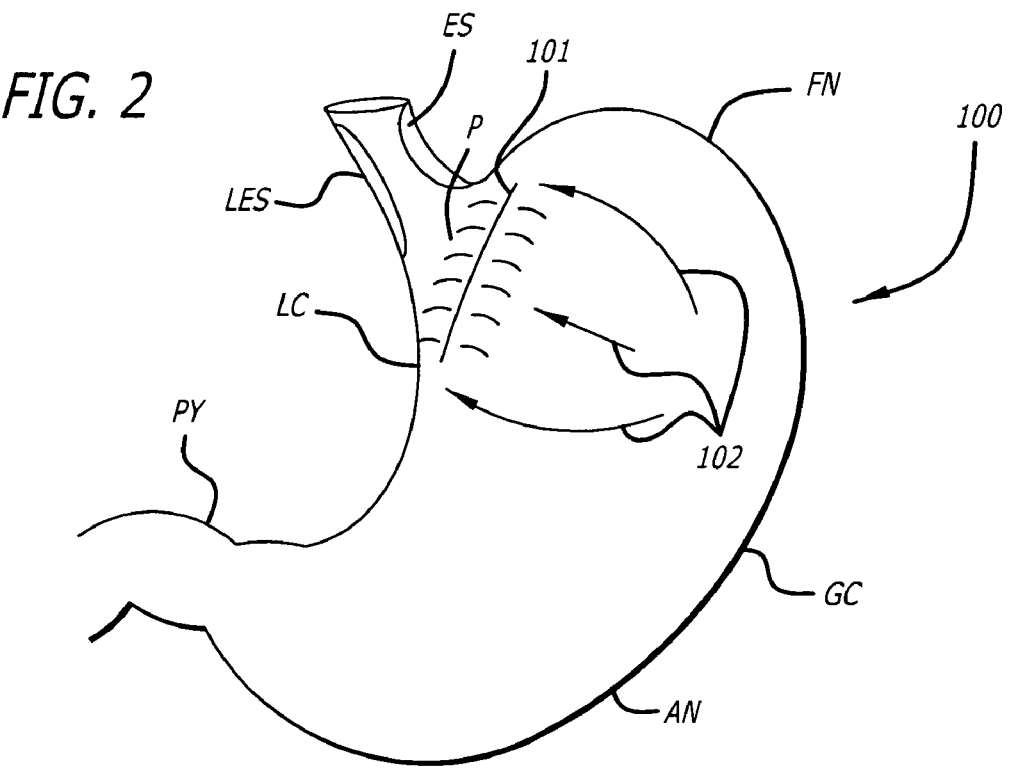
FIG. 2 depicts a schematic drawing showing a body organ with a partition or plication line placed to lessen the active reservoir of the gastric cavity.

FIG. 2 depicts an external view of a stomach organ 100 with an example of a partition or fastening line 101 placed in a location between the GEJ and the LC of the stomach 100. The partition 101 may be angled toward the LC relative to the GEJ to create a "pouch" (P) to achieve an overall reduction in volume of the active reservoir, i.e., the portion of the stomach 100 which is actively involved in food digestion. Arrows 102 represent the flow paths of potential refluxant that are prevented by the plication 101 from flowing upwards into the ES. In addition, pouch (P) operates to limit the volume of food or intake possible from the esophageal region (ES), and may therefore also effect weight loss in the target patient.

Figure 3:
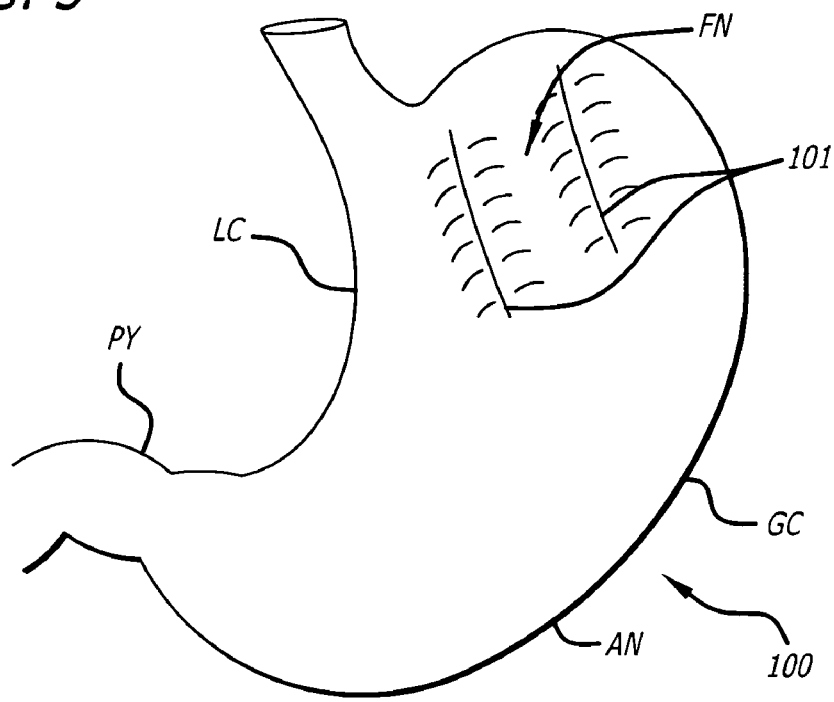
FIGS. 3, 5 and 6 depict schematic drawings showing a body organ with partitions or plications placed to reduce the volume capacity and to interfere with the constant fundic pressure urging food into the antral pump.
Figure 4A:
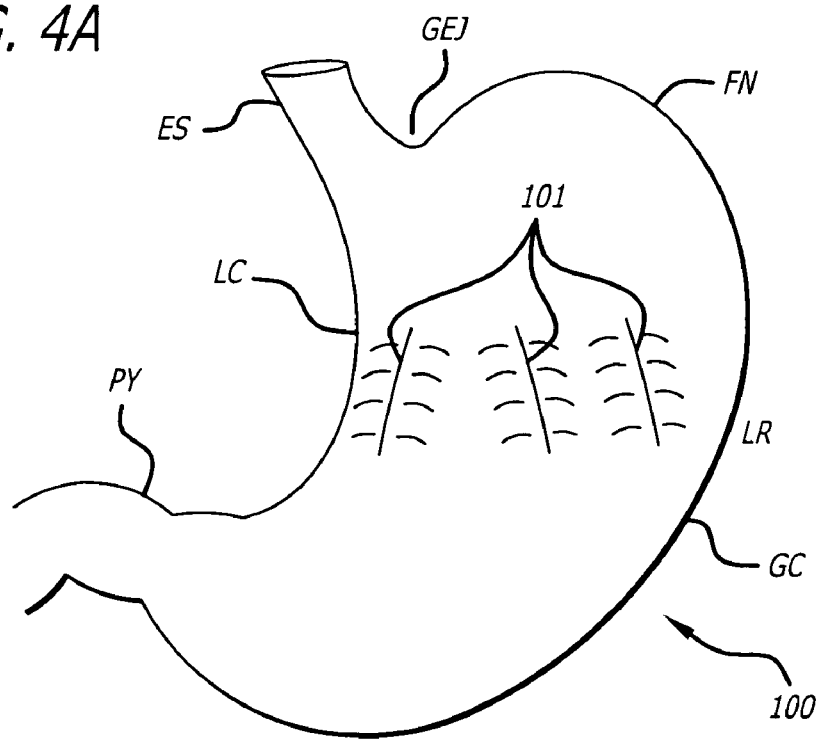
FIGS. 4A and 4B depict a schematic drawing showing a body organ with partitions or plications placed to disrupt the motility function of the organ.
Figure 4B:
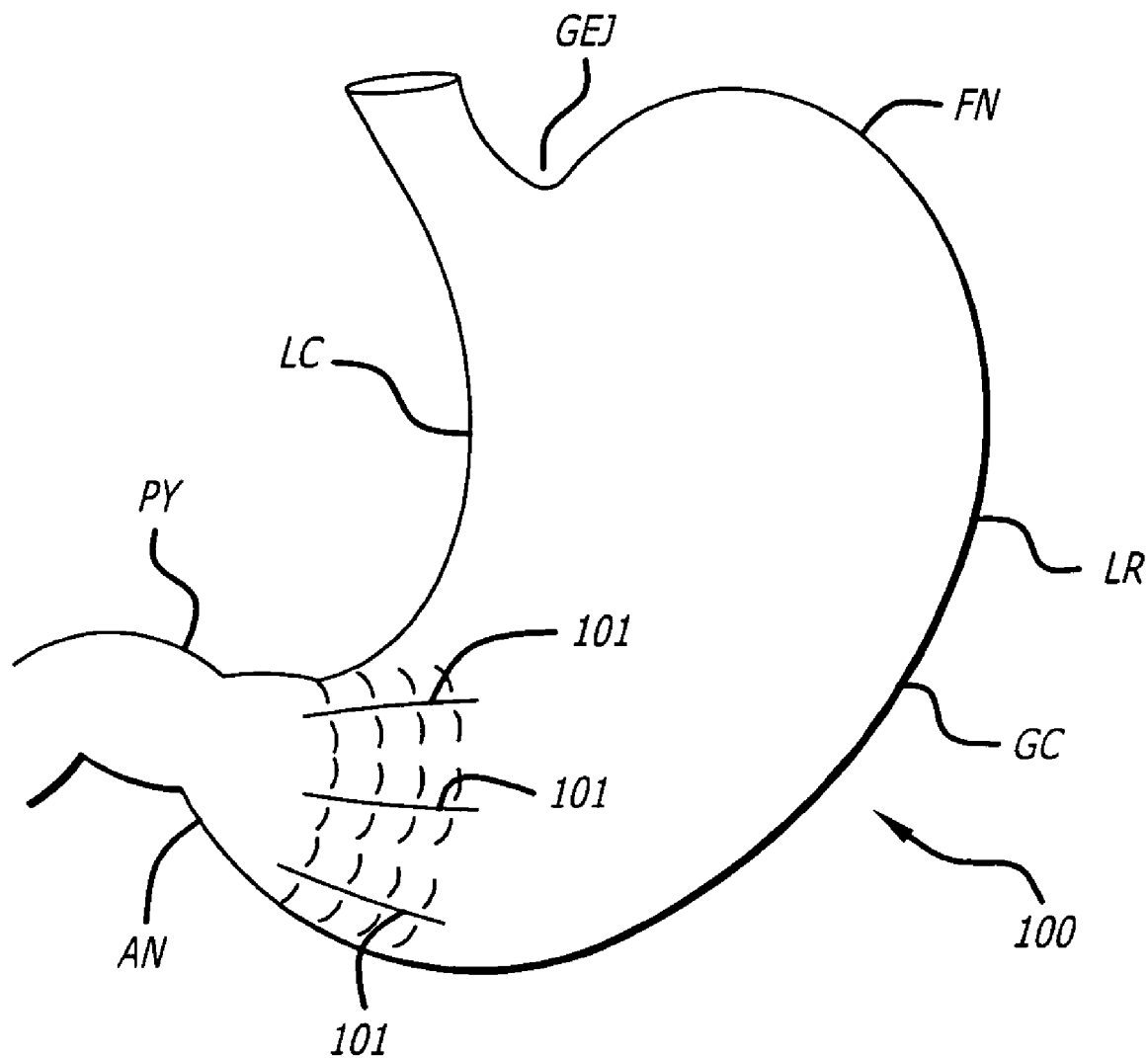

FIGS. 3 and 4 represent alternative placements of the partition or fastening line 101 to achieve various configurations of organ division. Each configuration may have a potential clinical application depending on the preference of the physician and clinical needs of the patient. In FIG. 3, plications may be placed within the fundic region FN and may function to both lessen distension of that region in response to food intake. The plications may also inhibit the fundic reservoir's ability to produce contractions by either attenuating or baffling the frequency and/or intensity of the contractions to slow digestion and reduce gastric emptying time. FIGS. 4A and 4B show yet another configuration of plications 101 located within the lower region LR of the stomach, which includes the lower body and the antrum AN region of the stomach 100. FIG. 4A shows plications 101 in the lower region (LR) and FIG. 4B shows plications 101 in the antrum (AN) region of the stomach 100. This placement is designed to disrupt or slow the contractile function of this region to slow gastric emptying time by interfering with the gastric pumping action and thereby enhance weight loss. As shown, the plications 101 may be aligned such that they point or extend angularly from the ES between the fundic region FN and a distal portion of the stomach 100. Plications 101 may extend partially within the stomach 100 or they may extend along a majority of a length of the stomach 100. Moreover, although only three plications 101 are shown, this is intended to be merely illustrative and a fewer or a greater number of plications may be utilized, depending upon the desired clinical results.

Figure 5:
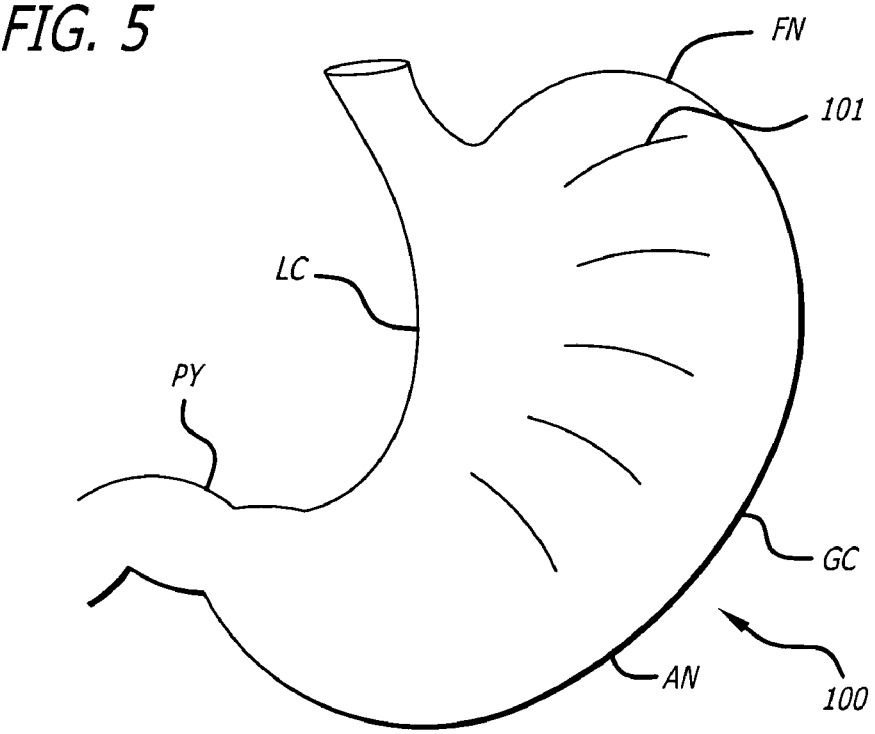
Figure 6:
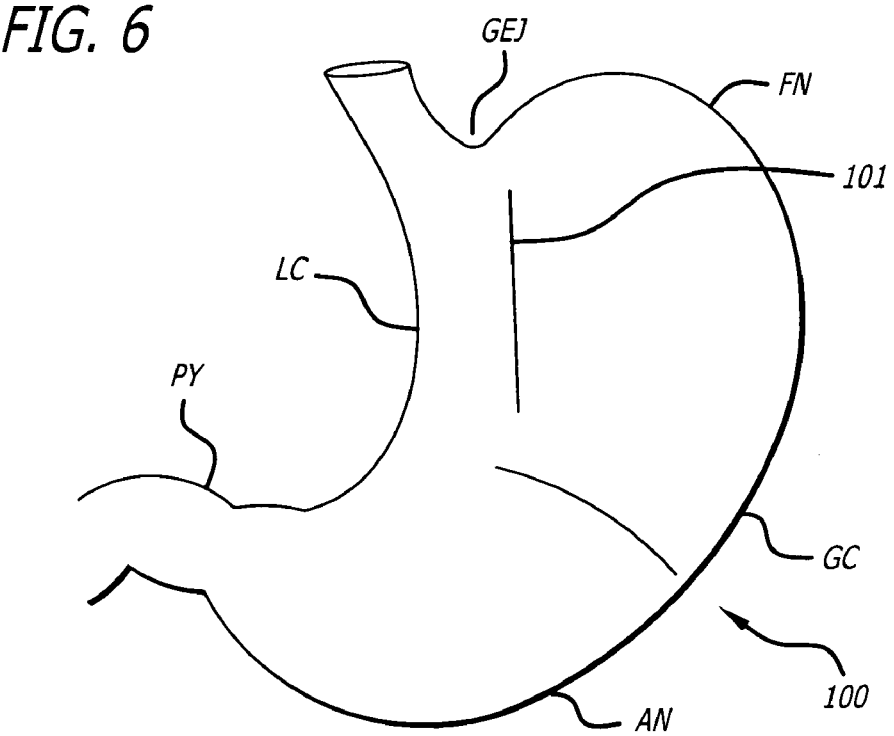

FIGS. 5 and 6 represent further alternative placements of partitions or fastening lines 101 within the stomach 100. The plications depicted in FIGS. 5 and 6 not only reduce organ volume, but also operate to effect organ motility, distension and pressure. The plications 101 shown in FIG. 5 may be created such that they extend a partial length within the stomach 101 in a "radial" pattern extending between the LC and the GC. The plications 101 shown in FIG. 6 may include a first plication 101 extending from the GEJ and extending a length towards the AN with a second plication extending partially between the LC and the GC from a distal end of the first plication.

Figure 7:
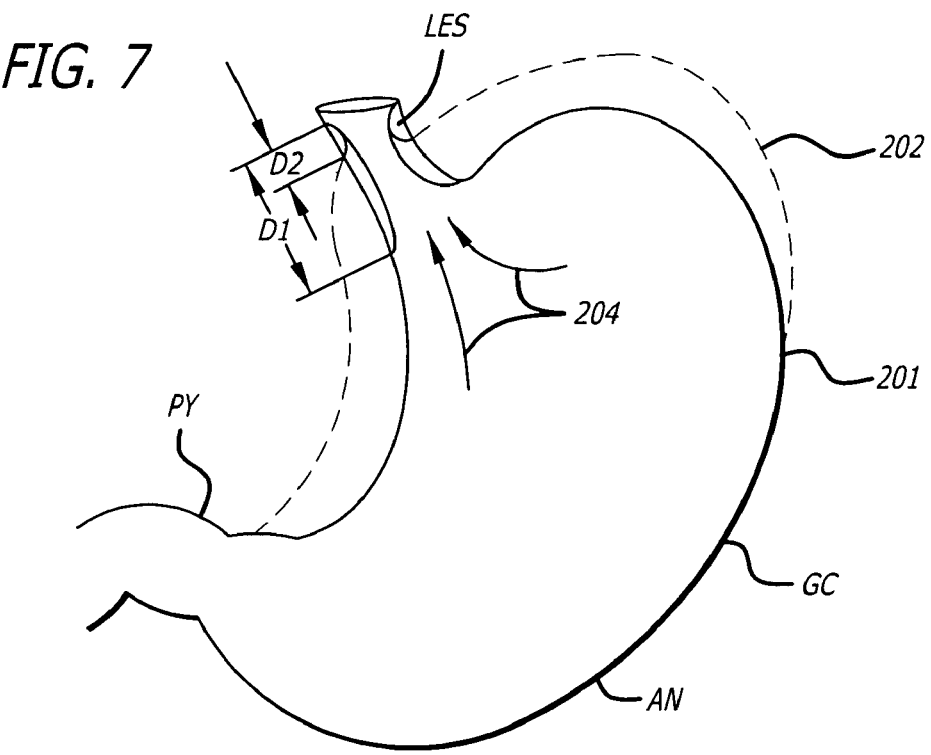
FIG. 7 depicts a schematic drawing showing distension of the gastric cavity and the resulting shortening of the LES.
Figure 8:
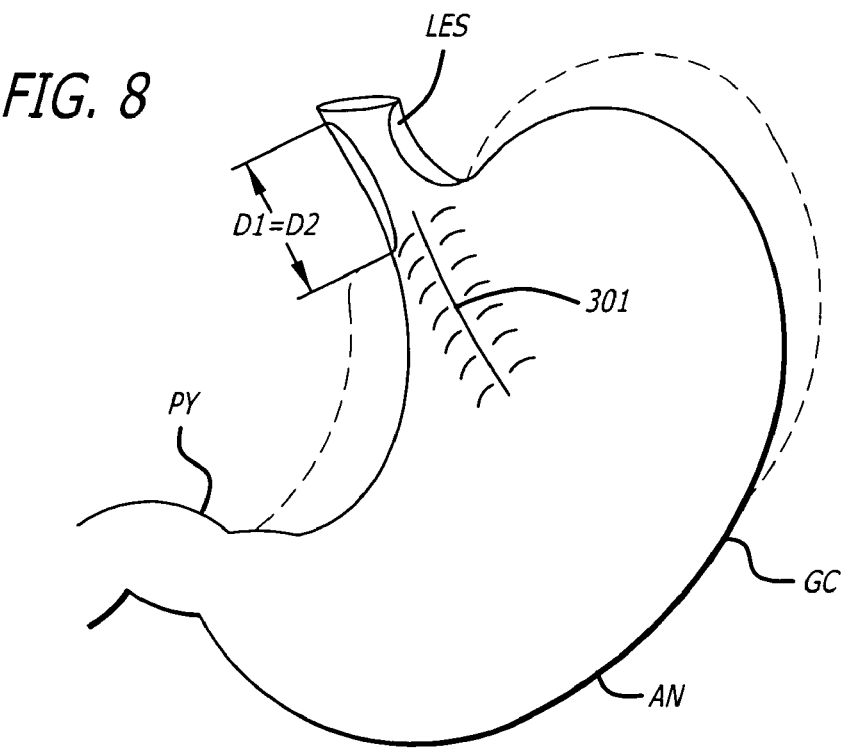
FIG. 8 depicts a schematic drawing showing a plication or partition placed near the LES to control the impact of distension of the gastric cavity on the LES.

In FIG. 7, stomach 100 is shown by the solid line 201 prior to intake of substances such as food or liquid. Measurement D1 represents the desired length of a healthy LES prior to food intake (in most cases, approximately 2 cm). Dotted line 202 depicts distension of the stomach following intake. Measurement D2 indicates shortening of the LES in response to the stomach 100 becoming distended. Once the LES shortens (e.g. in some cases to some length less than 2 cm), refluxant can then contact the esophageal region ES, as depicted by the arrows 204 which indicate refluxant flow paths, as the pressure created within the stomach 100 overwhelms the closing pressure of the shortened sphincter region D2. FIG. 8 depicts a stomach undergoing similar distension to that as shown in FIG. 7; however, plication 301 has been created at the base of the LES extending from the LES into the stomach. This placement of the plication 301 may limit the ability of the LES to shorten in response to gastric cavity distension. As a result, upon distension, D1 may approximately equal D2 after stomach distension where D2 may be greater than or equal to 2 cm. This measurement is approximately the length of a healthy functional LES, post stomach distension. Plication 301 is shown as extending partially into the stomach cavity; yet plication 301 may alternatively extend along a majority of the stomach cavity as well. The angle at which plication 301 extends relative to a longitudinal axis of the LES may also vary. For instance, plication 301 may be parallel to the longitudinal axis, or they may be relatively angled over a range suitable for preventing the LES from unrolling.

Figure 9:
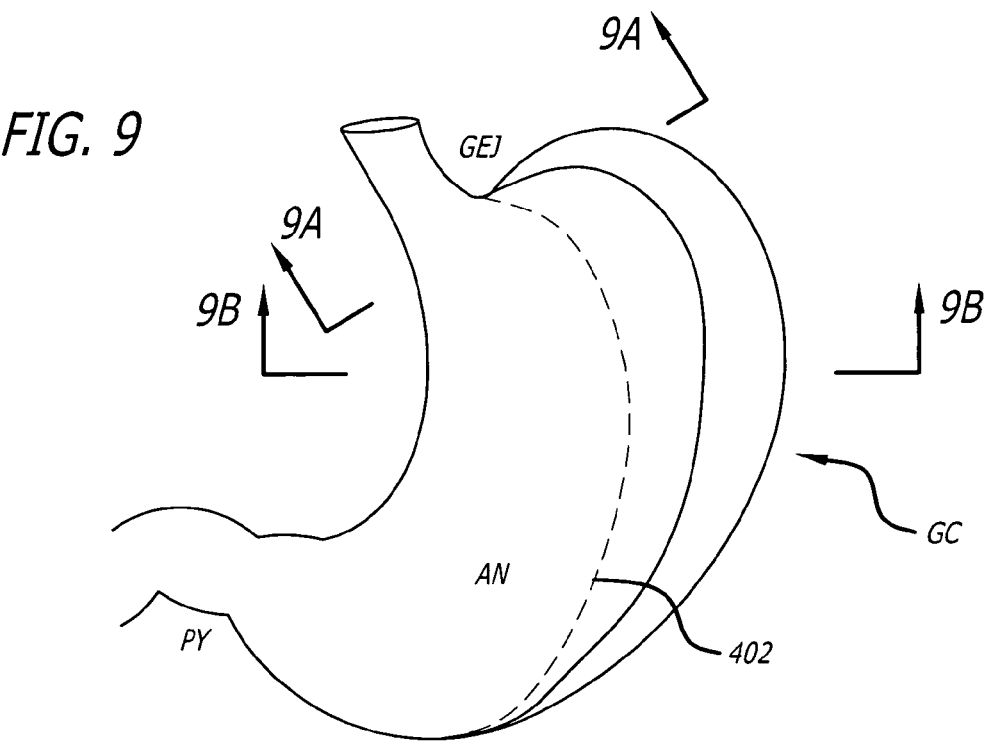
FIGS. 9 to 9B depict schematic drawings and cross-sectional views showing a plication of adjacent tissue placed along the length of the greater curve GC of the stomach to exclude the plicated portion from contact with the remaining tissue in the organ (for example to impair secretion of the hormone Ghrelin).
Figure 9A:
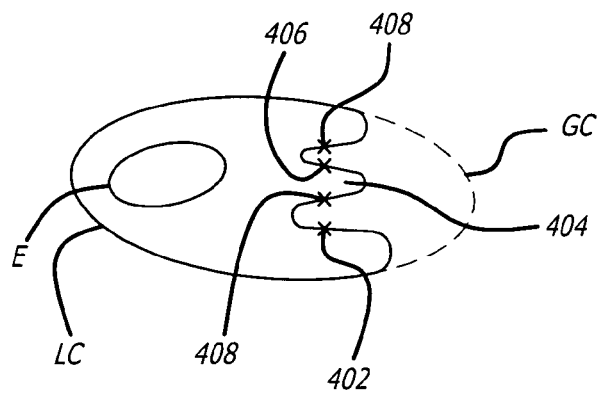

FIG. 9 depicts a schematic of a procedure where adjacent tissue (e.g., tissue from along the greater curve GC of the stomach) is acquired and plicated in a pattern configured to exclude certain portions of the stomach organ (e.g., fundus). Excluding certain portions, such as the fundus, from the other functioning regions of the stomach not only minimizes the overall volume of the organ so as to limit food intake, but also impairs the secretion of certain hormones, e.g., Ghrelin, which helps to control hunger levels. Suppression of Ghrelin or the exclusion of Ghrelin from the remaining stomach may suppress a hunger response in a person to facilitate weight loss. Plication line 402 can start at the GEJ and extend to below the antrum AN. Plication line 402 can terminate above the AN or extend further to the pylorus PY. FIG. 9A depicts cross section 9A-9A which shows a dotted line that represents the former location of the stomach GC prior to the region being acquired and plicated. FIG. 9A further depicts plication lines 402 and 406, and excluded tissue region 404 that, once plicated, is excluded from communication with the remaining organ volume along the length of the plication.

Figure 9B:
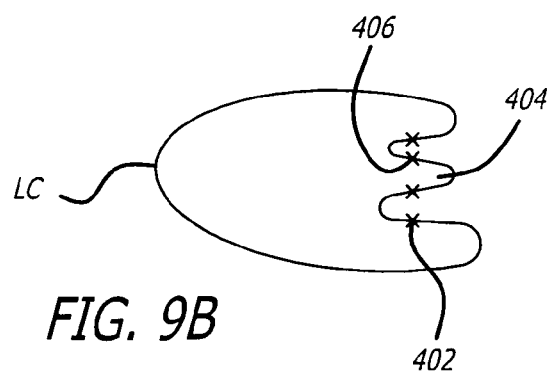

FIG. 9A illustrates two plication lines 402, 406 created adjacent to one another and creating tissue region 404. Although two plications are shown, a single plication may be created or three or more may be created depending upon the desired effects. Moreover, the plications may be adhered together via fasteners 408 along the length of the plications. Fasteners may include any number of types of fasteners ranging from staples, sutures, clips, helical screws, adhesives, etc. A further detailed discussion on fasteners is described in U.S. patent application Ser. Nos. 09/871,297 and 10/188,547, which have been incorporated herein by reference above. FIG. 9B shows another view in cross section 9B-9B of the plicated stomach from FIG. 9.

It is anticipated that the placement of partitions or fastening lines, as described above, may vary from those depicted herein as necessary for a physician to achieve a desired clinical effect, or to overcome variations in the anatomy of the patient. These configurations may include, additional plications, various angles along a plication relative to the anatomic location, such as 0.degree to 180.degree from the LC, or the GC, depending on the region to be effected. Such configurations that utilize the methods and devices of the present invention are contemplated to be within the scope of this disclosure.

We claim:

1. A method of inhibiting elongation of a proximal portion of a stomach, comprising:
   creating at least one plication between a first tissue region and a second tissue region from within the stomach;
   wherein the at least one plication extends from adjacent a lower esophageal sphincter to within the body of the stomach; and
   wherein a placement of the at least one plication is such that a consistent length of the lower esophageal sphincter prior to and after stomach distension is maintained.

2. The method of claim 1, wherein creating the at least one plication comprises configuring the plication to extend from a distal portion of the lower esophageal sphincter.

3. The method of claim 1, wherein creating the at least one plication comprises configuring the at least one plication to maintain the length of the lower esophageal sphincter at 2 cm or greater.

4. The method of claim 1 wherein creating the at least one plication comprises configuring the plication parallel to a longitudinal axis defined by the lower esophageal sphincter.

5. The method of claim 1 wherein creating the at least one plication comprises configuring the plication angled relative to a longitudinal axis defined by the lower esophageal sphincter.

6. The method of claim 1 wherein creating the at least one plication comprises configuring the plication to extend along a majority of the stomach.

* * * * *